(12) United States Patent
Vitek et al.

(10) Patent No.: US 8,932,237 B2
(45) Date of Patent: Jan. 13, 2015

(54) EFFICIENT ULTRASOUND FOCUSING

(75) Inventors: Shuki Vitek, Haifa (IL); Yoni Hertzberg, Givataim (IL)

(73) Assignee: InSightec, Ltd., Tirat Carmel (IL)

( * ) Notice: Subject to any disclaimer, the term of this patent is extended or adjusted under 35 U.S.C. 154(b) by 130 days.

(21) Appl. No.: 12/769,059

(22) Filed: Apr. 28, 2010

(65) Prior Publication Data

US 2011/0270136 A1 Nov. 3, 2011

(51) Int. Cl.
*A61H 1/00* (2006.01)
*A61N 7/02* (2006.01)
*A61B 19/00* (2006.01)
*A61N 7/00* (2006.01)

(52) U.S. Cl.
CPC .............. *A61N 7/02* (2013.01); *A61B 2019/505* (2013.01); *A61B 2019/5236* (2013.01); *A61N 2007/0065* (2013.01); *A61N 2007/0095* (2013.01)
USPC ........................................................... 601/2

(58) Field of Classification Search
CPC ........ A61N 7/00; A61N 7/02; A61H 23/0245
USPC ............................................................. 601/2
See application file for complete search history.

(56) References Cited

U.S. PATENT DOCUMENTS

| | | | |
|---|---|---|---|
| 2,795,709 A | 6/1957 | Camp | |
| 3,142,035 A | 7/1964 | Harris | |
| 3,942,150 A | 3/1976 | Booth et al. | |
| 3,974,475 A | 8/1976 | Burckhardt et al. | |
| 3,992,693 A | 11/1976 | Martin et al. | |
| 4,000,493 A | 12/1976 | Spaulding et al. | |
| 4,074,564 A | 2/1978 | Anderson | |
| 4,206,653 A | 6/1980 | LeMay | |
| 4,211,132 A | 7/1980 | Nichols, III et al. | |
| 4,307,613 A | 12/1981 | Fox | |
| 4,339,952 A | 7/1982 | Foster | |
| 4,454,597 A | 6/1984 | Sullivan | |
| 4,478,083 A | 10/1984 | Hassler et al. | |
| 4,505,156 A | 3/1985 | Questo | |
| 4,526,168 A | 7/1985 | Hassler et al. | |
| 4,537,074 A | 8/1985 | Dietz | |
| 4,549,533 A | 10/1985 | Cain et al. | |
| 4,554,925 A | 11/1985 | Young | |
| 4,662,222 A | 5/1987 | Johnson | |
| 4,817,614 A | 4/1989 | Hassler et al. | |
| 4,858,597 A | 8/1989 | Kurtze et al. | |

(Continued)

FOREIGN PATENT DOCUMENTS

DE 4345308 C2 2/2001
EP 0320303 6/1989

(Continued)

OTHER PUBLICATIONS

Fronheiser et al., "3D Acoustic Radiation Force Impulse (ARFI) Imaging Using a 2D Matrix Array: Feasibility Study," Ultrasonics Symposium, pp. 1144-1147 (Oct. 2006).

(Continued)

*Primary Examiner* — Tse Chen
*Assistant Examiner* — Hien Nguyen
(74) *Attorney, Agent, or Firm* — Morgan, Lewis & Bockius LLP

(57) ABSTRACT

Ultrasound focusing may be improved by combining knowledge of the target tissue and/or focusing arrangement with focus measurements.

3 Claims, 7 Drawing Sheets

(56) References Cited

U.S. PATENT DOCUMENTS

| | | |
|---|---|---|
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 5,197,475 A | 3/1993 | Antich et al. |
| 5,209,221 A | 5/1993 | Riedlinger |
| 5,211,160 A | 5/1993 | Talish et al. |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,435,312 A | 7/1995 | Spivey et al. |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,520,612 A | 5/1996 | Winder et al. |
| 5,526,814 A | 6/1996 | Cline et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,606,971 A | 3/1997 | Sarvazyan |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,728,062 A | 3/1998 | Brisken |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,784,336 A * | 7/1998 | Gopinathan et al. .......... 367/123 |
| 5,810,008 A | 9/1998 | Dekel et al. |
| 5,810,731 A | 9/1998 | Sarvazyan et al. |
| 5,873,845 A | 2/1999 | Cline et al. |
| 5,897,495 A | 4/1999 | Aida et al. |
| 5,904,659 A | 5/1999 | Duarte et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,135,960 A | 10/2000 | Holmberg |
| 6,193,659 B1 | 2/2001 | Ramamurthy et al. |
| 6,217,530 B1 | 4/2001 | Martin et al. |
| 6,242,915 B1 | 6/2001 | Hurd |
| 6,246,896 B1 | 6/2001 | Dumoulin et al. |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boernert et al. |
| 6,322,527 B1 | 11/2001 | Talish |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,433,464 B2 | 8/2002 | Jones |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich |
| 6,523,272 B1 | 2/2003 | Morales |
| 6,524,251 B2 | 2/2003 | Rabiner et al. |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,676,602 B1 | 1/2004 | Barnes et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 | 12/2006 | Halperin et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,429,248 B1 | 9/2008 | Winder et al. |
| 7,452,357 B2 | 11/2008 | Vlegele et al. |
| 7,505,805 B2 | 3/2009 | Kuroda |
| 7,505,808 B2 | 3/2009 | Anderson et al. |
| 7,507,213 B2 | 3/2009 | Schultheiss et al. |

(56) References Cited

U.S. PATENT DOCUMENTS

| | | | |
|---|---|---|---|
| 7,510,536 B2 | 3/2009 | Foley et al. | |
| 7,511,501 B2 | 3/2009 | Wexler | |
| 7,535,794 B2 | 5/2009 | Prus et al. | |
| 7,553,284 B2 | 6/2009 | Vaitekunas | |
| 7,603,162 B2 | 10/2009 | Danz et al. | |
| 7,611,462 B2 | 11/2009 | Vortman et al. | |
| 7,652,410 B2 | 1/2010 | Prus | |
| 7,699,780 B2 | 4/2010 | Vitek et al. | |
| 2001/0031922 A1 | 10/2001 | Weng et al. | |
| 2002/0016557 A1 | 2/2002 | Duarte et al. | |
| 2002/0035779 A1 | 3/2002 | Krieg et al. | |
| 2002/0082589 A1 | 6/2002 | Friedman et al. | |
| 2002/0095087 A1 | 7/2002 | Mourad et al. | |
| 2002/0111552 A1* | 8/2002 | Maor et al. | 600/439 |
| 2002/0161300 A1 | 10/2002 | Hoff et al. | |
| 2002/0188229 A1 | 12/2002 | Ryaby et al. | |
| 2003/0004439 A1 | 1/2003 | Pant et al. | |
| 2003/0060820 A1 | 3/2003 | Maguire et al. | |
| 2003/0187371 A1 | 10/2003 | Vortman et al. | |
| 2004/0030251 A1 | 2/2004 | Ebbini et al. | |
| 2004/0059265 A1 | 3/2004 | Candy et al. | |
| 2004/0068186 A1 | 4/2004 | Ishida et al. | |
| 2004/0122316 A1 | 6/2004 | Satoh | |
| 2004/0122323 A1 | 6/2004 | Vortman et al. | |
| 2004/0143187 A1 | 7/2004 | Biagi et al. | |
| 2004/0210134 A1 | 10/2004 | Hynynen et al. | |
| 2004/0210135 A1 | 10/2004 | Hynynen et al. | |
| 2004/0236253 A1 | 11/2004 | Vortman et al. | |
| 2004/0267126 A1 | 12/2004 | Takeuchi | |
| 2005/0033201 A1 | 2/2005 | Takahashi et al. | |
| 2005/0096542 A1 | 5/2005 | Weng et al. | |
| 2005/0131301 A1 | 6/2005 | Peszynski et al. | |
| 2005/0203444 A1 | 9/2005 | Schonenberger et al. | |
| 2005/0251046 A1 | 11/2005 | Yamamoto et al. | |
| 2006/0052661 A1 | 3/2006 | Gannot et al. | |
| 2006/0052701 A1 | 3/2006 | Carter et al. | |
| 2006/0052706 A1 | 3/2006 | Hynynen et al. | |
| 2006/0058678 A1* | 3/2006 | Vitek et al. | 600/459 |
| 2006/0106300 A1 | 5/2006 | Seppenwoolde et al. | |
| 2006/0173385 A1 | 8/2006 | Lidgren et al. | |
| 2006/0184034 A1 | 8/2006 | Haim et al. | |
| 2006/0184069 A1 | 8/2006 | Vaitekunas | |
| 2006/0206105 A1 | 9/2006 | Chopra et al. | |
| 2006/0229594 A1 | 10/2006 | Francischelli et al. | |
| 2007/0016039 A1 | 1/2007 | Vortman et al. | |
| 2007/0055140 A1 | 3/2007 | Kuroda | |
| 2007/0066897 A1 | 3/2007 | Sekins et al. | |
| 2007/0073135 A1 | 3/2007 | Lee et al. | |
| 2007/0098232 A1 | 5/2007 | Matula et al. | |
| 2007/0167781 A1 | 7/2007 | Vortman et al. | |
| 2007/0197918 A1 | 8/2007 | Vitek et al. | |
| 2007/0219470 A1 | 9/2007 | Talish et al. | |
| 2007/0239062 A1 | 10/2007 | Chopra et al. | |
| 2008/0027342 A1 | 1/2008 | Rouw et al. | |
| 2008/0031090 A1 | 2/2008 | Prus et al. | |
| 2008/0033278 A1 | 2/2008 | Assif | |
| 2008/0082026 A1 | 4/2008 | Schmidt et al. | |
| 2008/0108900 A1 | 5/2008 | Lee et al. | |
| 2008/0125660 A1 | 5/2008 | Yao et al. | |
| 2008/0183865 A1 | 7/2008 | Moreau-Gobard et al. | |
| 2008/0228081 A1 | 9/2008 | Becker et al. | |
| 2008/0312562 A1 | 12/2008 | Routh et al. | |
| 2009/0088623 A1 | 4/2009 | Vortman et al. | |
| 2009/0118619 A1 | 5/2009 | Oshiki | |
| 2010/0030076 A1 | 2/2010 | Vortman et al. | |
| 2010/0056962 A1 | 3/2010 | Vortman et al. | |
| 2010/0125193 A1 | 5/2010 | Zadicario | |
| 2010/0179425 A1 | 7/2010 | Zadicario | |
| 2010/0268088 A1 | 10/2010 | Prus et al. | |
| 2010/0274130 A1* | 10/2010 | Anand et al. | 600/439 |
| 2010/0318002 A1 | 12/2010 | Prus et al. | |
| 2011/0066032 A1 | 3/2011 | Vitek et al. | |
| 2011/0094288 A1 | 4/2011 | Medan et al. | |

FOREIGN PATENT DOCUMENTS

| | | |
|---|---|---|
| EP | 0558029 | 9/1993 |
| EP | 1132054 A1 | 9/2001 |
| EP | 1591073 | 11/2005 |
| EP | 1774920 A1 | 4/2007 |
| EP | 1790384 | 5/2007 |
| EP | 1936404 | 6/2008 |
| FR | 2806611 A1 | 9/2001 |
| JP | 5-92008 | 4/1993 |
| JP | 7-184907 | 7/1995 |
| JP | 7-231895 | 9/1995 |
| JP | 7-313518 | 12/1995 |
| JP | 11313833 A | 11/1999 |
| JP | 00/166940 | 6/2000 |
| JP | 01/516075 | 9/2001 |
| JP | 02/530145 | 9/2002 |
| WO | WO-9100059 A1 | 1/1991 |
| WO | WO-95/14505 | 6/1995 |
| WO | WO-9852465 A1 | 11/1998 |
| WO | WO-0031614 A1 | 6/2000 |
| WO | WO-01/58337 | 8/2001 |
| WO | WO-0166189 A1 | 9/2001 |
| WO | WO-0180709 A2 | 11/2001 |
| WO | WO-02/43805 | 6/2002 |
| WO | WO-02/44753 | 6/2002 |
| WO | WO-02058791 A1 | 8/2002 |
| WO | WO-03/013654 A1 | 2/2003 |
| WO | WO-03097162 A2 | 11/2003 |
| WO | WO-03098232 A2 | 11/2003 |
| WO | WO-2004/093686 | 11/2004 |
| WO | WO-2005058029 A2 | 6/2005 |
| WO | WO-2006018837 A2 | 2/2006 |
| WO | WO-2006025001 A1 | 3/2006 |
| WO | WO-2006047649 A1 | 8/2006 |
| WO | WO-2006/119572 | 11/2006 |
| WO | WO-2007/051066 | 5/2007 |
| WO | WO-2007073551 A1 | 6/2007 |
| WO | WO-2008/039449 | 4/2008 |
| WO | WO-2008050278 A1 | 5/2008 |
| WO | WO-2008075203 A2 | 6/2008 |
| WO | WO-2008119054 A1 | 10/2008 |
| WO | WO-2009055587 A1 | 4/2009 |
| WO | WO-2009/081339 | 7/2009 |
| WO | WO-2009/094554 | 7/2009 |
| WO | WO-2010/058292 | 5/2010 |
| WO | WO-2010/082135 | 7/2010 |
| WO | WO-2010/119340 | 10/2010 |
| WO | WO-2010/143072 | 12/2010 |
| WO | WO-2011/013001 | 2/2011 |
| WO | WO-2011/024074 | 3/2011 |

OTHER PUBLICATIONS

Wu et al., "MRImaging of Shear Waves Generated by Focused Ultrasound," Magnetic Resonance in Medicine, vol. 43, pp. 111-115 (2000).

Heikkila et al., "Simulations of Lesion Detection Using a Combined Phased Array LHMI-Technique," Ultrasonics, IPC Science and Technology Press Ltd., vol. 48, No. 6-7, pp. 568-573 (Nov. 2008).

International Search Report and Written Opinion mailed Nov. 10, 2011 for International Application No. PCT/IB2011/001375 (13 pages).

McDonnald et al. "Usefulness of MR Imaging-Derived Thermometry and Dosimetry in Determining the Threshold for Tissue Damage INduced by Thermal Surgery in Rabbits," Radiology, vol. 216, No. 2000 pp. 517-523 (2000).

Suprijanto et al. "Displacement Correction Scheme for MR-Guided Interstitial Laser Therapy," Ellis RE, Peters TM (Eds.): MiCCAI , LNCS 2879, pp. 399-407 (2003).

Shmatukha et al. "Correction of Proton Resonance Frequencey Shift Temperature Maps for Magnetic Field Disturbances Caused by Breathing," Physics in Medicine and Biology, vol. 51, No. 18 pp. 4689-4705 (2006).

De Senneville et al., "An Optimised Multi-Baseline Approach for On-Line MR-Temperature Monitoring on Commodity Graphics Hardware," Biomedical Imaging, pp. 1513-1516 (2008).

(56) References Cited

OTHER PUBLICATIONS

Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).
Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).
Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).
Chen et al., "MR Acoustic Radiation Force Imaging: Comparison of Encoding Gradients."
Cline et al., "Focused US system for MR imaging-guide tumor ablation," Radiology, v. 194, No. 3, pp. 731-738 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (1998).
de Senneville et al., "Real-time adaptive methods for treatment of mobile organs by MRI-controlled high-intensity focussed Ultrasound," Magnetic Resonance in Medicine 57:319-330 (2007).
Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. on Therapeutic Ultrasound.
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
International Preliminary Report on Patentability in International Patent Application No. PCT/IB2004/001512, mailed Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, mailed Dec. 20, 2005.
International Search Report and Written Opinion in International Patent Application No. PCT/IB2005/002413, mailed Nov. 22, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/001079, mailed Dec. 10, 2007.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.
International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. on Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. on Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Mougenot et al., "MR monitoring of the near-field HIFU heating," 8th Intl. Symp. on Therapeutic Ultrasound, edited by E.S. Ebbini, U. of Minn. (Sep. 2009).
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.
International Search Report and Written Opinion in International Patent Application No. PCT/IB2010/000189, mailed Jun. 1, 2010.
International Search Report for PCT/IB03/05551 completion date Mar. 2, 2004 (5 pages).
International Search Report and Written Opinion in Internation Patent Application No. PCT/IB2010/000971, mailed Jul. 29, 2010 (9 pages).
First Office Action for 200680029730.8 PRC (7 pages).
McGough et al., "Direct Computation of Ultrasound Phased-Array Driving Signals from a Specified Temperature Distribution for Hyperthermia," IEEE Transactions on Biomedical Engineering, vol. 39, No. 8, pp. 825-835 (Aug. 1992).

\* cited by examiner

EFFICIENT ULTRASOUND FOCUSING

FIELD OF THE INVENTION

The present invention relates, generally, to systems and methods for ultrasound focusing. In particular, various embodiments are directed to efficient methods of focusing a phased array of ultrasound transducer elements, using both model-based computations and measurements of focus quality to adjust the relative phases of the transducer elements.

BACKGROUND

Focused ultrasound (i.e., acoustic waves having a frequency greater than about 20 kilohertz) can be used to image or therapeutically treat internal body tissues within a patient. For example, ultrasonic waves may be used to ablate tumors, eliminating the need for the patient to undergo invasive surgery. For this purpose, a piezo-ceramic transducer is placed externally to the patient, but in close proximity to the tissue to be ablated (the "target"). The transducer converts an electronic drive signal into mechanical vibrations, resulting in the emission of acoustic waves (a process hereinafter referred to as "sonication"). The transducer may be shaped so that the waves converge in a focal zone. Alternatively or additionally, the transducer may be formed of a plurality of individually driven transducer elements whose phases (and, optionally, amplitudes) can each be controlled independently from one another and, thus, can be set so as to result in constructive interference of the individual acoustic waves in the focal zone. Such a "phased-array" transducer facilitates steering the focal zone to different locations by adjusting the relative phases between the transducers, and generally provides the higher a focus quality and resolution, the greater the number of transducer elements. Magnetic resonance imaging (MRI) may be utilized to visualize the focus and target in order to guide the ultrasound beam.

The relative phases at which the transducer elements need to be driven to result in a focus at the target location depend on the relative location and orientation of the transducer surface and the target, as well as on the dimensions and acoustic material properties (e.g., sound velocities) of the tissue or tissues between them (i.e., the "target tissue"). Thus, to the extent the geometry and acoustic material properties are known, the relative phases (and, optionally, amplitudes) can be calculated, as described, for example, in U.S. Pat. No. 6,612,988 (filed Dec. 15, 2000), U.S. Pat. No. 6,770,031 (filed Aug. 26, 2002), and U.S. Pat. No. 7,344,509 (filed Apr. 9, 2004), as well as U.S. patent application Ser. No. 12/425, 698 (filed on Apr. 17, 2009), the entire disclosures of which are hereby incorporated by reference. In practice, however, knowledge of these parameters is often too incomplete or imprecise to enable high-quality focusing based on computations of the relative phases alone. For example, when ultrasound is focused into the brain to treat a tumor, the skull in the acoustic path may cause aberrations that are not readily ascertainable. In such situations, treatment is typically preceded by an auto-focusing procedure in which, iteratively, an ultrasound focus is generated at or near the target, the quality of the focus is measured (using, e.g., thermal imaging or acoustic radiation force imaging (ARFI)), and experimental feedback is used to adjust the phases of the transducer elements to achieve sufficient focus quality.

The number of sonications in this procedure is typically at least three times the number of individually controlled transducer elements, and even more sonications may be needed to overcome measurement noise. The auto-focusing procedure may thus take a substantial amount of time, which may render it impracticable or, at the least, inconvenient for a patient. Further, during the auto-focusing sonications, ultrasound energy is inevitably deposited into the tissue at and surrounding the target, potentially damaging healthy tissue. While the effect of pre-therapeutic sonications may be minimized by employing an imaging technique that requires only low acoustic intensity (e.g., ARFI), it is generally desirable to limit the number of sonications prior to treatment. Accordingly, there is a need for more efficient ways of focusing a phased array of transducer element to create a high-quality ultrasound focus.

SUMMARY

The present invention provides, in various embodiments, systems and methods for focusing ultrasound by adjusting the phases and, optionally, amplitudes of a phased array of transducer elements based on a combination of (i) a-priori knowledge about the relative location and/or orientation between the transducer surface and the target, the dimensions and/or acoustic material properties of the target tissue, and/or any quantities derived from these parameters (hereinafter collectively referred to as a "sonication model"), and (ii) experimental feedback about the focus quality. Using focus measurements to adjust the transducer elements may improve focus quality over purely computational approaches, while employing computations based on a sonication model may reduce the number of sonications (and, thus, the time and energy needed to achieve a given focus quality).

In some embodiments, transducer elements are grouped into sub-arrays, and each sub-array is treated, for purposes of experimental phase adjustments, as a single element. Such grouping reduces the number of independently controllable elements and, consequently, the optimization time and energy. While, in general, fewer elements result in lower resolution and, hence, lower focus quality, this undesirable effect may be avoided or minimized by "smart grouping" based on the sonication model (e.g., based on the incidence angle of ultrasound from a sub-array onto a target tissue interface, i.e., an outer surface of the target tissue or an interface between multiple layers of the target tissue). Smart grouping involves keeping the array resolution (i.e., the number of independently controllable elements per unit area) high in regions where finer adjustments may be needed.

In some embodiments, a model of the target tissue is developed, and uncertainties in the model (e.g., uncertainties about the values of certain geometric or material parameters) are captured in one or more variable model parameters. The model parameters are then varied discretely over ranges that are expected to include the unknown true parameter values, and for each discrete set of parameter values, the phases (and amplitudes) of the transducer elements are computed for a given focus target, the transducers are driven accordingly, and the resulting focus quality is measured. The set of parameter values that yields the best focus is adopted, and may subsequently be used to compute the relative transducer element phases for therapeutic sonications of the target. Often, relatively few sonications—compared with the number required for auto-focusing without a-priori knowledge—will suffice to find an approximation of the model parameter values that results in an acceptable focus quality.

In a first aspect, a method of focusing a phased array of ultrasound transducer elements into a target tissue, in accordance with various embodiments, involves grouping the transducer elements into sub-arrays based on a sonication model, and determining relative phases of the transducer elements within each sub-array. Further, the method includes driving the transducer elements of the sub-arrays at the respective relative phases to generate sub-foci, determining whether the sub-foci constructively interfere, and, if not, adjusting the phases of the transducer elements to cause constructive interference of the sub-foci.

The sonication model may include a geometric parameter indicative of a relative arrangement between the phased array and the target tissue; a target focus location; and/or one or more material parameters and/or geometric parameters of the target tissue, which may be obtained by measurements using, e.g., MRI or computer tomography. Grouping may be based on incidence angles of ultrasound emitted from the transducer elements on a target tissue interface. The relative phases of the transducer elements within a sub-array may be computed based on the sonication model, and/or may be determined experimentally by driving the transducer elements of the sub-array so as to generate a sub-focus, measuring a quality of the sub-focus, and adjusting the relative phases to improve the quality of the sub-focus.

Determining whether the sub-foci constructively interfere may involve determining whether the sub-foci are in phase and/or whether they are co-located. If the sub-foci are not in phase, the phases of the transducer elements may be adjusted by applying phase shifts of equal magnitude to the transducer elements within each sub-array, and choosing the phase shifts applied to respective sub-arrays so as to bring the sub-foci in phase. If the sub-foci are not co-located, adjusting the phases of the transducer elements may include applying phase gradients across the transducer elements of each sub-array so as to co-locate the sub-foci. In some embodiments, the determination whether the sub-foci constructively interfere includes measuring a quality of a global focus formed by the sub-foci, e.g., by measuring a tissue displacement associated with the global focus, using magnetic-resonance acoustic radiation force imaging (MR-ARFI).

In a second aspect, various embodiments provide a method of focusing a phased array of ultrasound into a target tissue using a model of the target tissue that includes one or more model parameters (e.g., the velocity of sound). The method involves, for each of a plurality of value sets for the model parameter(s), the steps of computing relative phases of the transducer elements based (at least in part) on the model and a target focus location in the target tissue, driving the transducer elements at the computed relative phases so as to generate an ultrasound focus at the target focus location, and measuring the quality of the focus (e.g., by measuring a tissue displacement associated with the focus using ARFI). Among the plurality of value sets, the set associated with the highest focus quality is selected. The transducer elements may then be driven at relative phases computed based on the model, the selected model parameter value set, and the target focus location.

The method may further include the step of obtaining the model of the target tissue, for instance, by measuring a material property and/or a geometric characteristic of the target tissue (using, e.g., MRI or computer tomography). In some embodiments, the model includes a plurality of model parameters, and each of the value sets comprises a value for each of the model parameters. In other embodiments, the model includes a single model parameter, and each of the value sets comprises a value for the single model parameter.

In a third aspect, various embodiments are directed to a system for focusing ultrasound into a target tissue using a sonication model. The system includes a phased array of ultrasound transducer elements for generating an ultrasound focus in the target tissue, a system (e.g., an MRI system) for imaging the ultrasound focus, and a control facility in communication with the MRI system and the phased array of transducer elements. The control facility is configured to receive data associated with the sonication model, compute relative phases of the transducer elements based at least in part on the data, drive the transducer elements at the relative phases so as to generate the ultrasound focus, and adjust the relative phases, based at least in part on an image of the ultrasound focus, so as to improve the ultrasound focus.

In some embodiments, the control facility is configured to group the transducer elements into sub-arrays and compute relative phases of the transducer elements within each sub-array. Further, the control facility may be configured to adjust the relative phases so as to cause constructive interference of sub-foci generated by the sub-arrays.

In some embodiments, the data includes multiple value sets for at least one model parameter of the sonication model. The control facility may be configured to compute relative phases of the transducer elements and drive the transducer elements at the relative phases sequentially for the multiple value sets of the model parameter(s). Further, the control facility may be configured to measure a quality of the focus for each of the multiple value sets and to select, among the multiple value sets, the set associated with the highest focus quality.

In a third aspect, various embodiments are directed to an ultrasound focusing system for use in connection with an imaging system. The system includes a phased array of ultrasound transducer elements for generating an ultrasound focus in the target tissue; and a control facility configured to (i) receive data associated with a sonication model, (ii) based at least in part on the data, compute relative phases of the transducer elements, (iii) drive the transducer elements at the relative phases so as to generate the ultrasound focus, and (iv) based at least in part on an image of the ultrasound focus provided by the imaging system, adjust the relative phases so as to improve the ultrasound focus. The imaging system may be a magnetic resonance imaging system.

BRIEF DESCRIPTION OF THE DRAWINGS

The foregoing will be more readily understood from the following detailed description of the invention in conjunction with the drawings, wherein.

DETAILED DESCRIPTION

Figure 1:
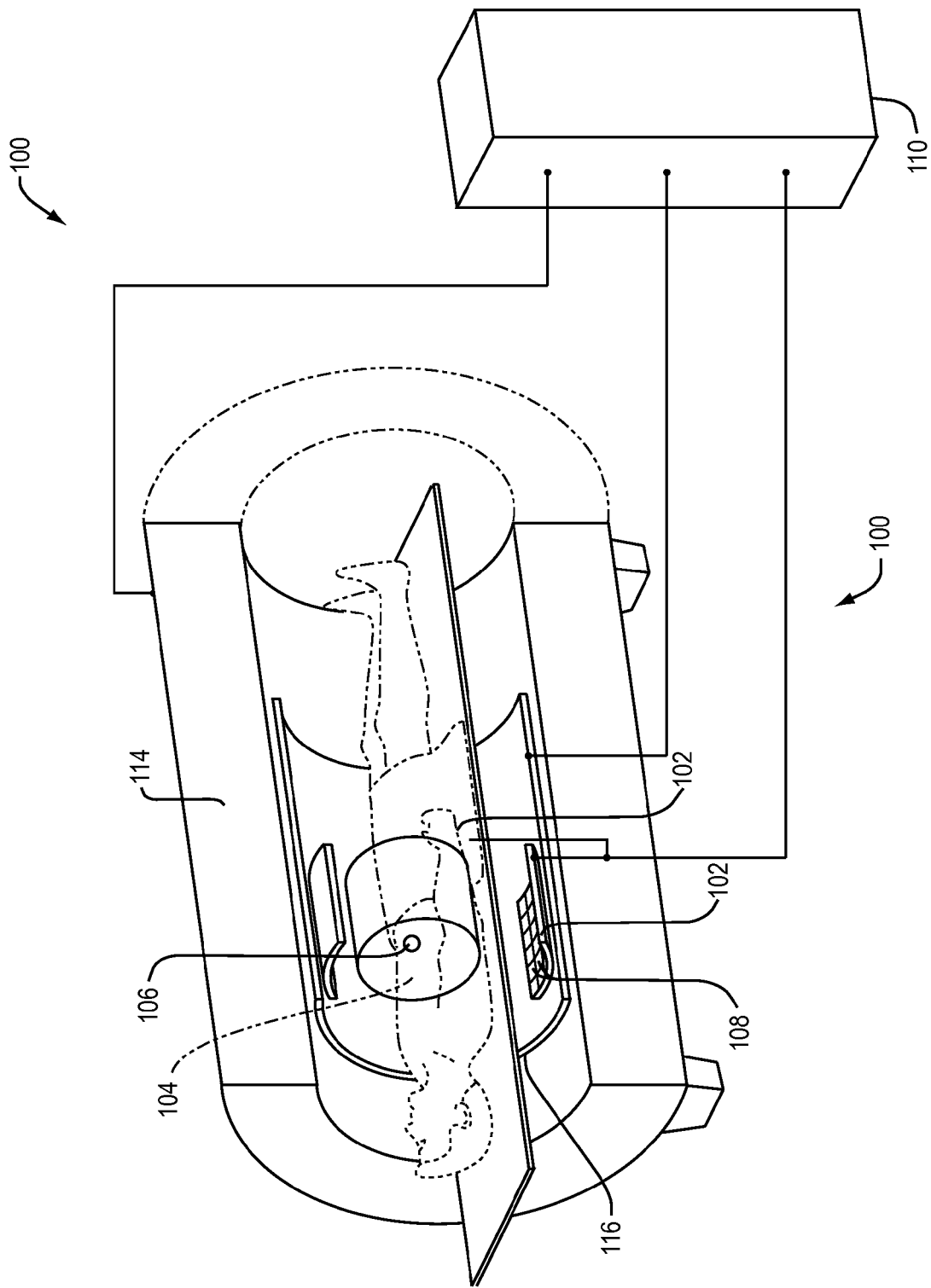
FIG. 1 is a schematic drawing illustrating a magnetic-resonance-guided focused ultrasound system (MRgFUS) in accordance with various embodiments.

FIG. 1 illustrates schematically an exemplary MRgFUS 100 in accordance with various embodiments of the invention. The system includes an ultrasound transducer 102, which is disposed near the torso 104 of a patient and directed towards a target 106 in a region of interest ("ROI") inside the patient. The transducer 102 may comprise a one- or two-dimensional array (i.e., a row or a matrix) of individually controllable transducer elements 108. In other embodiments, the transducer elements 108 may be arranged in a non-coordinated fashion, i.e., they need not be spaced regularly or arranged in a regular pattern. The transducer may have a curved (e.g., spherical or parabolic) shape, as illustrated, or may include one or more planar or otherwise shaped sections. Its dimensions may vary, depending on the application, between millimeters and tens of centimeters. The transducer elements 108 may be piezoelectric ceramic elements. Piezocomposite materials, or generally any materials capable of converting electrical energy to acoustic energy, may also be used. To damp the mechanical coupling between the elements 108, they may be mounted on the housing using silicone rubber or any other suitable damping material.

The transducer elements 108 are separately controllable, i.e., they are each capable of emitting ultrasound waves at amplitudes and/or phases that are independent of the amplitudes and/or phases of the other transducers. A control facility 110 in communication with the array serves to drive the transducer elements 108. For n transducer elements 108, the control facility 110 may contain n control circuits, each comprising an amplifier and a phase delay circuit and driving one of the transducer elements. The control facility 110 may split a radio frequency (RF) input signal, typically in the range from 0.1 MHz to 4 MHz, to provide n channels for the n control circuits. The control facility may be configured to drive the individual transducer elements 108 at the same frequency, but at different phases and different amplitudes so that they collectively produce a focused ultrasound beam. The control facility 110 may also include additional circuitry and switches that allow subsets of the transducer elements to be grouped into sub-arrays, and the elements within one sub-array to be driven at the same amplitude and phase.

The control facility 110 desirably provides computational functionality, which may be implemented in software, hardware, firmware, hardwiring, or any combination thereof, to compute the required phases and amplitudes for a desired focus location. For example, the control facility 110 may receive data indicative of the desired focus location (i.e., the target) relative to the ultrasound transducer, and account for the respective distances between each transducer element and the target, and the associated travel times of the acoustic waves that originate at the various transducer elements, in computing the phases. If the sum of the transducer element phase and the phase acquired between the transducer element and the target (i.e., the product of the frequency and the travel time of the wave, modulo $2\pi$) is the same for all elements, the waves from the different transducer elements constructively interfere at the target. Since the travel time of a wave depends on the velocity of sound between the transducer element and the target, which is generally different for different tissues, the phase computation may be based on a model of the target tissue that contains information about the thicknesses and sound velocities of the various tissue layers that form the target tissue.

In general, the control facility may include several separable apparatus, such as a frequency generator, a beamformer containing the amplifier and phase delay circuitry, and a computer (e.g., a general-purpose computer) performing the computations and communicating the phases and amplitudes for the individual transducer elements 108 to the beamformer(s). Such systems are readily available or can be implemented without undue experimentation.

The MRgFUS system 100 further includes an MRI apparatus in communication with the control facility 110. The apparatus may include a cylindrical electromagnet 114, which generates a static magnetic field within a bore thereof. During medical procedures, the patient may be placed inside the bore on a movable support table, and positioned such that an imaging region encompassing the ROI (e.g., a particular organ) falls within a region where the magnetic field is substantially uniform. The magnetic field strength within the uniform region is typically between about 1.5 and about 3.0 Tesla. The magnetic field causes hydrogen nuclei spins to align and precess about the general direction of the magnetic field. An RF transmitter coil 116 surrounding the imaging region emits RF pulses into the imaging region, causing some of the aligned spins to oscillate between a temporary high-energy non-aligned state and the aligned state. This oscillation induces RF response signals, called the magnetic-resonance (MR) echo or MR response signals, in a receiver coil, which may, but need not, be the transmitter coil 116. The MR response signals are amplified, conditioned, and digitized into raw data using an image processing system (which may be implemented, e.g., in control facility 110), and further transformed into arrays of image data by methods known to those of ordinary skill in the art. Based on the image data, the target 106 (e.g., a tumor) is identified. The ultrasound transducer 102 is then driven so as to focus ultrasound into (or near) the treatment region.

To confirm the location and measure the quality of the focus, the focus may be visualized using one of a number of MR-based imaging techniques, such as, e.g., thermal MRI or MR-ARFI. Because MR-ARFI generally requires lower ultrasound energies during alignment and calibration procedures than other methods, and the ultrasound intensity preceding the actual treatment should be minimized to avoid damage to tissue outside the target, MR-ARFI is typically preferred. In MR-ARFI, a transducer is driven so as to focus an ultrasound wave pulse into the body at or near the target. The ultrasound wave exerts acoustic radiation pressure onto the material along its path. At the focus, where the waves converge, this pressure is highest, resulting in a temporary local displacement of the material in the longitudinal direction and/or in shear waves that propagate radially away from the focus. Thus, the ultrasound pressure creates a displacement field that directly reflects the acoustic field. The displacement field may be visualized by applying transient-motion or displacement-sensitizing magnetic field gradients to the imaging region by gradient coils, which are part of standard MRI systems and are typically located near the cylindrical electromagnet 114. When the ultrasound pulse is applied in the presence of such gradients, the resulting displacement is directly encoded into the phase of the MR response signal. For example, the gradient coils and transducer may be configured such that the ultrasound pulse pushes material near the focus towards regions of the magnetic field with higher field strengths. In response to the resulting change in the magnetic field, the phase of the MR response signal changes proportionally, thereby encoding in the signal the displacement caused by the ultrasound radiation pressure.

Figure 2A:
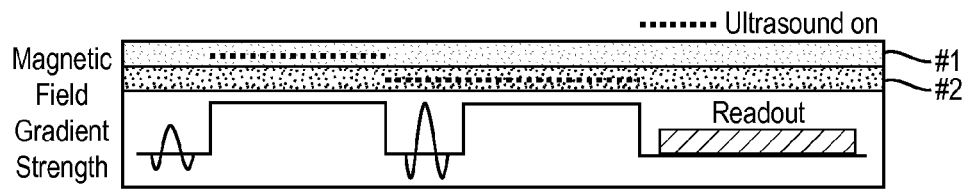
FIGS. 2A-2C illustrate several magnetic-resonance ARFI sequences in accordance with various embodiments.
Figure 2B:
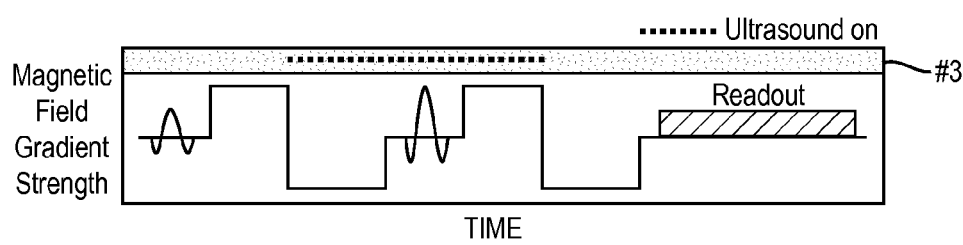
Figure 2C:
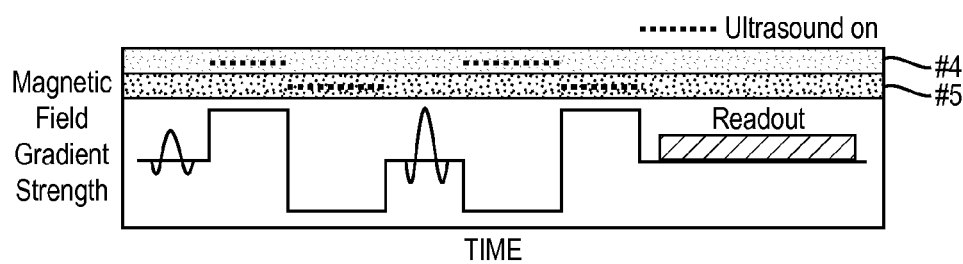

To achieve high image contrast, the ultrasound pulse, encoding gradients, and RF pulse are precisely timed with respect to each other according to a suitable displacement-encoding sequence. FIGS. 2A-2C illustrate five exemplary MR-ARFI sequences that may be used in embodiments of the invention. These sequence diagrams illustrate the order in which the displacement-encoding magnetic field gradients (thin solid lines), ultrasound pulses (dotted lines), and RF pulses (thick solid lines) appear in time. Three different field gradient sets are shown: two single lobes (a), repeated bipolars (b), and inverted bipolars (c). For gradient set (a), ultrasound may be applied during either the first or the second lobe. Similarly, for gradient set (c), ultrasound may be applied during the first or the second halves of the bipolars. In general, MR-ARFI sequences utilize magnetic field gradients that are synchronized with the ultrasound pulses. In preferred embodiments, a sequence like the repeated bipolar sequence (b) shown in FIG. 2B may be used. The imaging sequence may be programmed into the control facility 110. The control facility 110 may then send trigger signals to the ultrasound transducer and the MRI hardware to ensure correct timing between the signals.

Figure 3A:
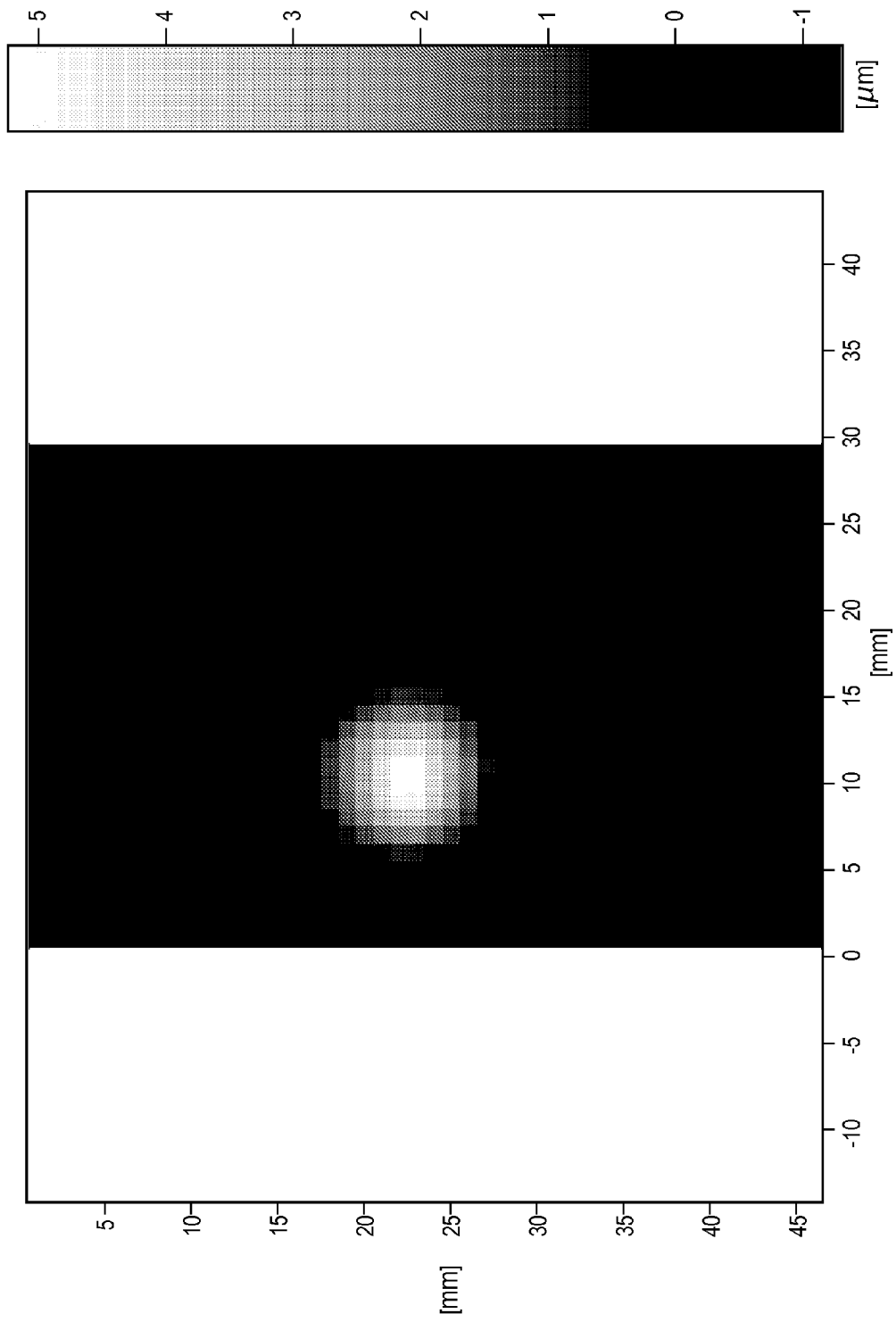
FIG. 3A is an image of material displacements in an ultrasound focus region in accordance with some embodiments.
Figure 3B:
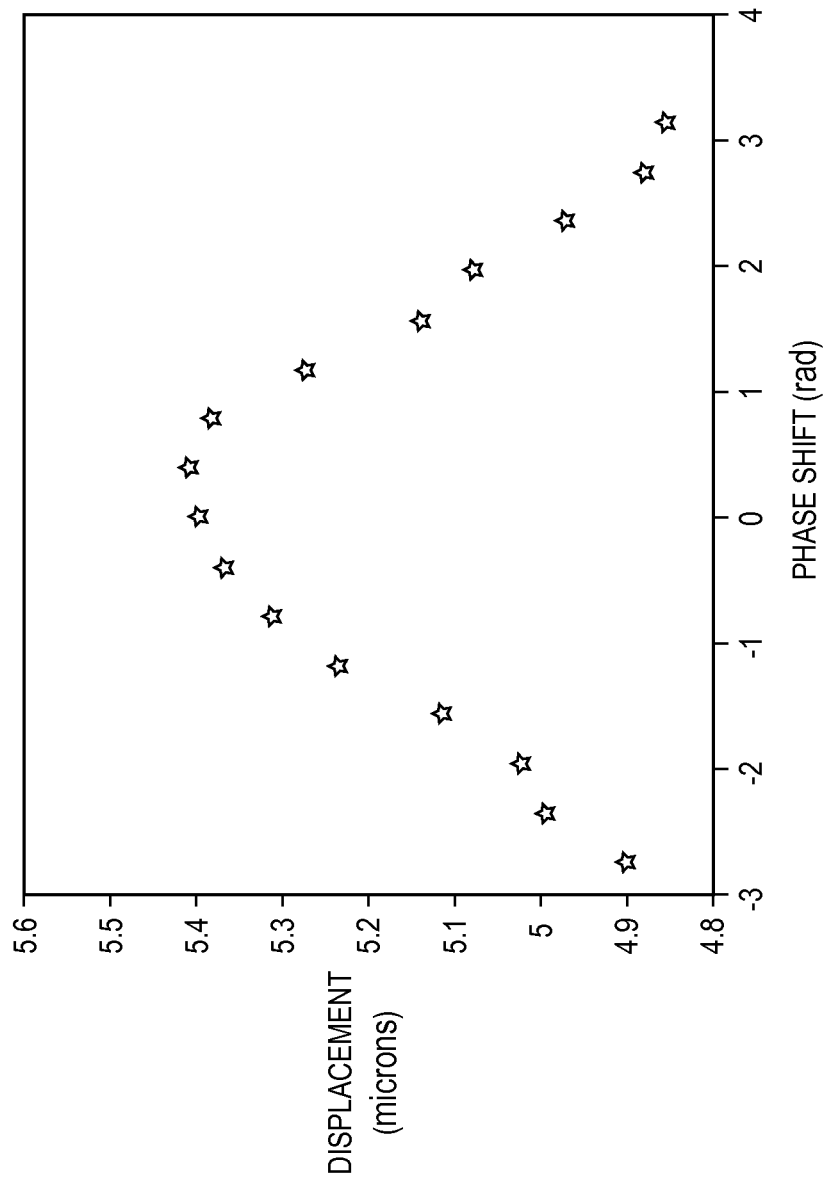
FIG. 3B is a graph illustrating material displacement in the focus center as a function of the phase of an individual transducer element, as it may be used in calibrations methods in accordance with various embodiments.

An example of an MR-ARFI image of an ultrasound focus region is shown in FIG. 3A. As shown, the material displacement with respect to an equilibrium position varies between about −1 µm and 5 µm. In general, the stronger the acoustic field intensity, the greater will be the maximum displacement at the center of the focus. The acoustic field intensity, in turn, is maximized when the individually controlled portions of the transducer (i.e., the elements within a transducer segments and/or the various segments) emit acoustic waves that are all in phase at the focus position. If a transducer element is out of phase with respect to the others, the focus intensity in the center decreases. This relationship can be exploited to optimize the focus, and thus to map and adjust the transducer elements and/or segments, as detailed further below. Assuming, for example, that all but one of the transducer elements of a segment are properly configured, the correct phase of the last element can be determined by tuning the phase over a full cycle (e.g., between −π and +π), measuring for each phase the displacement in the focus center, and then setting the phase to the value corresponding to the maximum displacement. FIG. 3B depicts the results of such an adjustment procedure. In the illustrated example, the material displacement over the full phase cycle of one element varies between about 4.85 µm and about 5.4 µm. The maximum displacement occurs at about 0.12 rad. Consequently, the focus intensity and quality can be improved by introducing a phase shift of 0.12 rad for the tested transducer element.

MR-ARFI may be used to "auto-focus" an ultrasound beam (i.e., to iteratively improve the focus quality of a pre-focused beam based on experimental feedback) in advance of the therapeutic application of ultrasound. Consider, for example, the treatment of a brain tumor with ultrasound. A transducer for such an application is usually large; it may surround a wide area of the skull and comprise a large number of elements (e.g., 1000). In preparation for treatment, the transducer is typically placed in a stable position relative to the patient's head, and the transducer elements are then activated at relative phases based on the sonication geometry (which generally includes the relative position and orientation of transducer and the target tissue, as well as the target location). Optionally, phase corrections may be applied to the transducer elements to compensate for tissue aberrations, which are mostly caused by the intervening skull tissue and which may vary significantly with location. The phase corrections may be computed based on skull-imaging data obtained, for example, through computer tomography or MRI, which provide estimates of the local skull bone thickness and density. Often, such computational correction for skull-based aberrations results in a noticeable, yet insufficient improvement of the focus quality. The focus may be optimized with an auto-focusing procedure, in which low-energy ultrasound is focused at (or near) the target, and a quantity correlated to the focus quality (e.g., the peak displacement caused by radiation force) is measured.

Auto-focusing typically involves a systematic series of sonications for various transducer phasing combinations. Without further information, it may take about 3000 or more sonications to optimize the focus of an array with 1000 elements. However, a-priori information capable of reducing the required number of sonications may be available. Such a-priori information may include a model of the target tissue, which may provide detailed information about the components of the target tissue (such as various tissue layers), their relative arrangement, and the associated material types, densities, and structures, and/or various material parameter values. A target tissue model may be developed based on images of the target tissue, and/or generally known or experimentally determined material parameters and physical properties of certain tissue types and/or interfaces between tissue layers (such as, e.g., coefficients of reflection at an interface between bone and soft tissue). In addition, a-priori information may include relevant parameters of the sonication geometry, i.e., the location and orientation of the transducer with respect to the target tissue. The sonication geometry may be known from mechanical constraints (such as, e.g., a rigid transducer structure that is placed in contact with the target tissue), or measured using fiducials or sensors embedded in the transducer, such as MR tracking coils or position sensors (e.g., tilt indicators, ultrasound, or optical encoders). Using such a-prior information, the relative phases between transducer elements that are required for a particular target are often predictable in the vicinity of a particular location at the transducer. On the other hand, the relative phases between groups of transducers that are further apart from one another may require adjustment.

Figure 4:
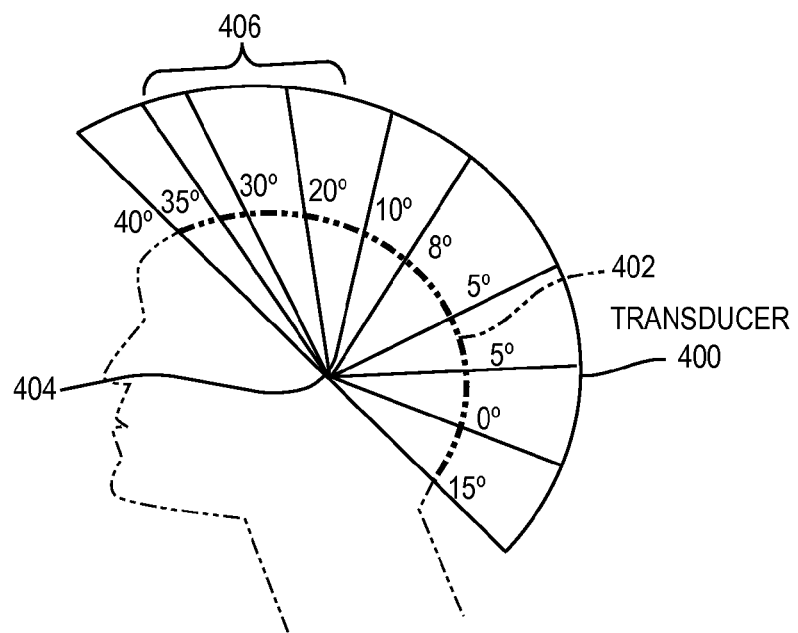
FIG. 4 is a schematic drawing of a transducer arrangement for brain tumor treatment, illustrating smart grouping of transducer elements in accordance with one embodiment.

FIG. 4 illustrates schematically an exemplary sonication geometry for ultrasound focusing into the brain. A curved transducer 400 is placed above a patient's skull 402 and driven so as to focus ultrasound from many directions onto a target 404. In this arrangement, the incidence angle of ultrasound onto the skull varies greatly, between 0° (perpendicular incidence) and about 40°. The incidence angle has been found to be a major determining factor for the reliability of phase corrections computed with a sonication model derived from computer tomography or MRI data. For incidence angles below about 15° and above about 35°, the phase corrections are usually highly reliable. For incidence angles in a critical range between about 15° and about 35° (corresponding to region 406 in FIG. 4), experimental adjustment of phases is desirable. Therefore, one approach to combining a-priori knowledge with experimental feedback involves segmenting the transducer array (or, in other words, grouping the transducer elements) into sub-arrays according to incidence angle. Sub-arrays associated with incidence angles that do not allow for reliable prediction may consist of only few or, in the extreme case, individual transducer elements, whereas sub-arrays associated with low (e.g., <15° or high (e.g., >35° incidence angles typically include many elements—and generally the higher the degree of predictability, the more elements may be combined in a sub-array.

Figure 5:
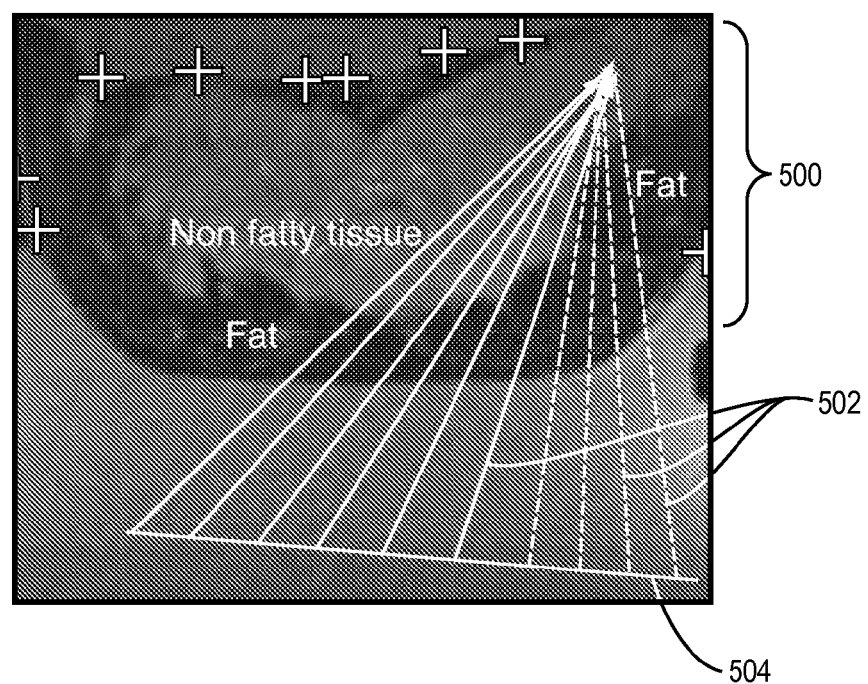
FIG. 5 is an MR image of a female breast, illustrating tissue properties relevant to focusing ultrasound for breast cancer treatment in accordance with one embodiment.

As a person of skill in the art will appreciate, the smart-grouping approach outlined above may be modified depending on the particular application. For example, the critical range of incidence angles may differ from the one used in the above example. Further, the grouping of transducer elements need not be based on incidence angles at all, but may, generally, be based on other parameters of the sonication model that affect the reliability of computationally determined transducer element phases. For instance, the grouping may be based on the predominant type of tissue that an acoustic wave traverses to reach the focus location. Tissue type is relevant, for example, in the treatment of breast cancer, as illustrated in FIG. 5. The figure shows an MRI image of the breast 500 of a woman in prone position, which is to be treated from below as indicated by the arrows 502. A set of many MRI images would be needed for three-dimensional information. The ultrasound beam, which originates from a transducer surface 504, generally passes through both fatty and non-fatty tissues, which have different sound velocities. These variations in velocity may cause aberrations that disturb the focus. The aberrations may be reduced by calculating time delays for each transducer element from the MRI image(s), and compensating for the time delays with corresponding phase shifts. To increase the accuracy of the calculated time delays, the transducer may be partitioned into sub-arrays whose acoustic waves travel through mostly fatty or mostly non-fatty tissue, respectively.

Figure 6A:
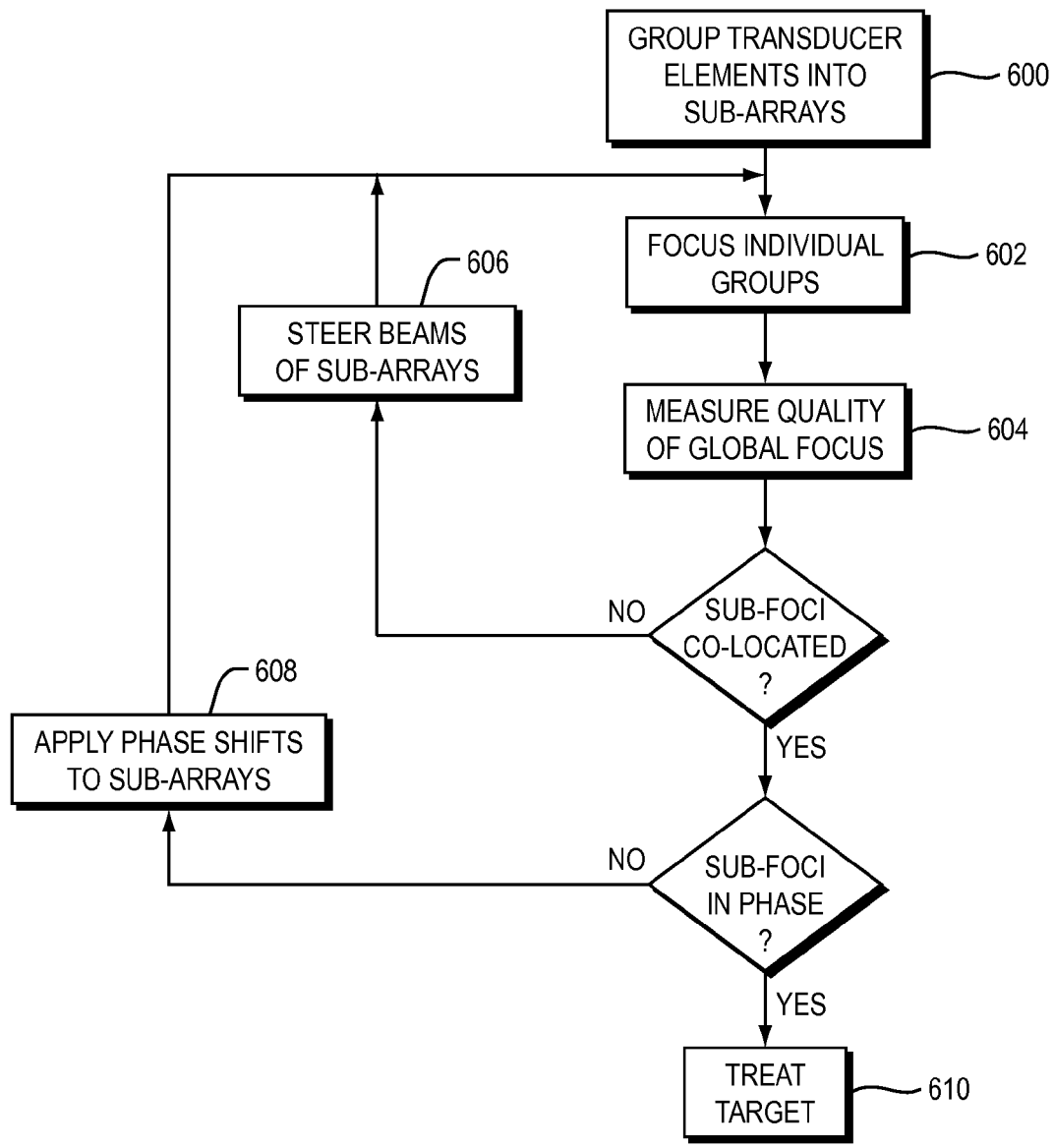
FIG. 6A is a flow chart illustrating an ultrasound focusing method involving smart grouping of transducer element in accordance with one embodiment.

FIG. 6A illustrates, in a flow chart, a method of focusing a transducer array using smart grouping. After the transducer elements have been grouped into sub-arrays (step 600), each sub-array may be driven so as to create a discrete sub-focus at or near the target, such as, e.g., target 404 in FIG. 4 (step 602). The relative phases (and amplitudes) of the elements within a sub-array may be computed based on the sonication model (i.e., information about the local geometry and tissue properties). In some embodiments, the sub-foci of one or more sub-arrays are further improved using auto-focusing with focus quality feedback. For example, in the context of focusing ultrasound into the brain as shown in FIG. 4, instead of sub-dividing the transducer into individual transducer elements at locations corresponding to incidence angles in the critical regime (where a high resolution is generally required), the transducer elements may be grouped into a sub-array, their relative phases adjusted using, e.g., MR-ARFI, and the sub-array subsequently treated as only one element.

Once the relative phases within the sub-arrays are properly set, the quality of the global focus, which is the superposition of the sub-foci, may be measured (step 604), e.g., using MR-ARFI. An optimal global focus is achieved when the sub-foci constructively interfere, i.e., when they are co-located and in phase. In many (but not all) applications, adjusting the overall phase of each sub-array will suffice to achieve constructive interference because creating the sub-foci at the target location will already guarantee their geometric overlap. If the sub-foci are not sufficiently co-located (due to a deviation of their location from the target location), their relative positions may be adjusted by steering the respective ultrasound beams to the desired location (step 606). Steering involves applying phase gradients to the sub-arrays, which changes the relative phases between transducer elements within a sub-array, but in a constrained way that preserves most of the information about relative phases. To bring the sub-foci in phase, phase shifts may be applied to the sub-arrays (step 608). (Applying a phase shift to a sub-array involves applying that phase shift to each element within the sub-array.) When the focus quality is sufficient, i.e., the sub-foci constructively interfere, the transducer may be employed in treating the target (step 610).

A different approach to using information of the target tissue and supplementing it with experimental feedback on the focus quality involves modeling the target tissue with variable parameters. Such a target-tissue model may account for the fact that some parameters are better known than others. For example, the MR image shown in FIG. 5 provides good information about the thickness of the various tissues, such as water, fatty tissue, and non-fatty tissue, along the acoustic rays originating at different transducer locations. However, while the sound velocity of water is well-known, the sound velocities of fatty and non-fatty tissues are only known within comparatively large intervals of uncertainty, and generally vary between patients. Thus, the time delays for the different acoustic rays are also uncertain. The degree of uncertainty may, however, be reduced indirectly by computing the relative phases for different values of the sound velocities within the known ranges, and comparing the quality of the resulting foci (again, using MR-ARFI or another technique to measure focus parameters indicative of the quality). The sound velocity values that result in the best focus (among the ones measured and compared) may then be assumed to be good approximations of the true sound velocities.

More generally, focus quality feedback may be used to supplement an incomplete target tissue model with N unknown parameters. For each unknown parameter $v_i$, the interval of uncertainty may be sampled with $k_i$ values. For example, in the breast treatment case, where N=2, the sound velocity of fatty tissue and the sound velocity of non-fatty tissue may each be sampled with $k_1=k_2=5$ values. Exploring the entire discrete two-dimensional space of parameter values will then require 25 sonications—significantly fewer than would typically be needed to adjust the transducer element phases without using any a-priori information about the target tissue. Determining values of tissue model parameters using MR-ARFI feedback may thus, in certain applications, provide a viable alternative to smart grouping for the purpose of achieving high focus quality with a reduced number of calibration sonications.

Figure 6B:
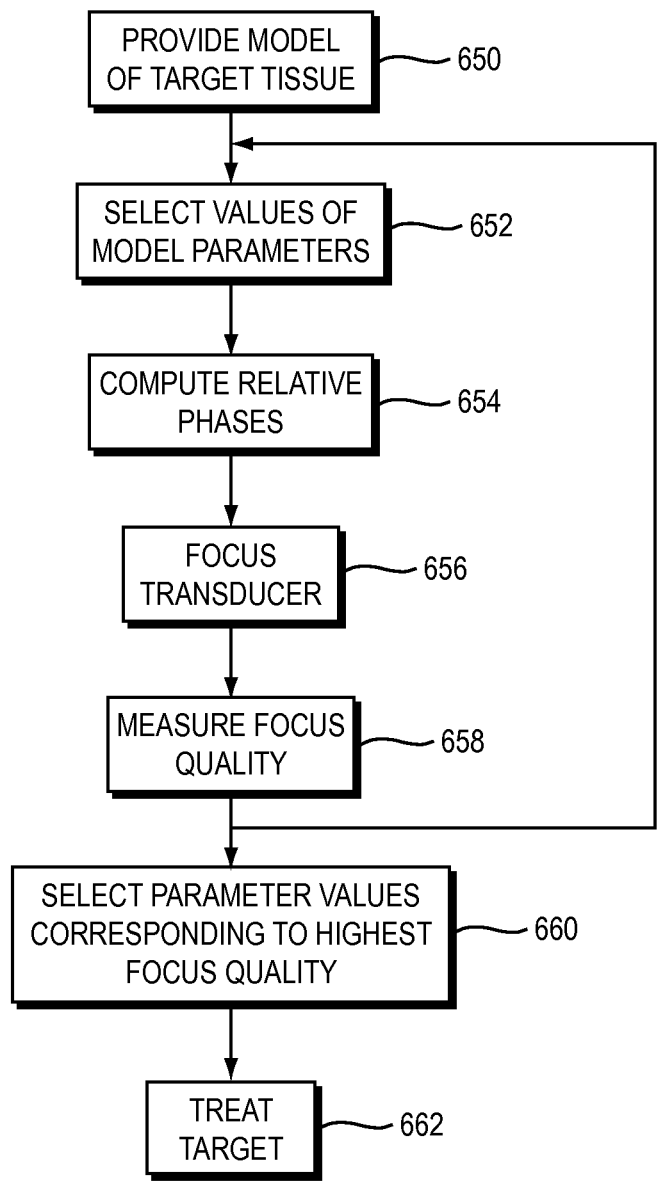
FIG. 6B is a flow chart illustrating an ultrasound focusing method involving experimentally determining parameter values of a target tissue model in accordance with one embodiment.

FIG. 6B illustrates a method of using a target tissue model in combination with experimental feedback to improve the quality of an ultrasound focus. The first step 650—providing the model—may be accomplished, for example, by imaging the target tissue with the MRI apparatus to determine the thicknesses and locations of various tissue layers, and supplying this information to the control facility. Then, model parameters that are not known a priori are assigned arbitrary values within ranges in which the true values are expected to lie (step 652), the relative phases are adjusted based on the model and the selected parameter values (step 654), and the transducer is focused (step 656) and the focus quality measured (step 656). These steps are repeated for multiple value sets of the parameters. The focus qualities for different value sets are then compared, and the value set that corresponds to the best focus is selected. Once the target tissue model has thus been supplemented, the transducer may be driven in accordance with the model to sonicate and thereby treat the target (step 662).

Although the present invention has been described with reference to specific details, it is not intended that such details should be regarded as limitations upon the scope of the invention, except as and to the extent that they are included in the accompanying claims.

What is claimed is:
1. A system for focusing ultrasound into a target tissue using a sonication model, the system comprising:
   a phased array of ultrasound transducer elements configured to generate an ultrasound focus in the target tissue;
   an imaging system configured to image the ultrasound focus; and in communication with the imaging system and the phased array of transducer elements, a control facility configured to set relative phases between the transducer elements so as to create a global focus from a plurality of sub-foci, the facility being configured to (i) receive data associated with the sonication model, the data comprising a parameter including at least one of an incidence angle or a predominant type of the target tissue and affecting a reliability of computational phase determinations, (ii) based at least in part on the parameter, group the transducer elements into sub-arrays, at least one of the sub-arrays comprising multiple transducer elements, and compute relative phases of the transducer elements within each sub-array, (iii) drive the transducer elements of the sub-arrays at the respective computed relative phases so as to generate the ultrasound sub-foci, each of which is associated with one of the sub-arrays, and (iv) based at least in part on an image of the ultrasound sub-foci, adjust the relative phases so as to cause constructive interference of the ultrasound foci, thereby generating the global focus.

2. The system of claim 1, wherein the imaging system is a magnetic resonance imaging system.

3. A system for use in connection with an imaging system and for focusing ultrasound into a target tissue using a sonication model, the system comprising:

a phased array of ultrasound transducer elements configured to generate an ultrasound focus in the target tissue; and a control facility configured to set relative phases between the transducer elements so as to create a global focus from a plurality of sub-foci, the facility being configured to (i) receive data associated with the sonication model, the data comprising a parameter including at least one of an incidence angle or a predominant type of the target tissue and affecting a reliability of computational phase determinations, (ii) based at least in part on the parameter, group the transducer elements into sub-arrays, at least one of the sub-arrays comprising multiple transducer elements, and compute relative phases of the transducer elements within each sub-array, (iii) drive the transducer elements of the sub-arrays at the respective computed relative phases so as to generate the ultrasound sub-foci, each of which is associated with one of the sub-arrays, and (iv) based at least in part on an image of the ultrasound sub-foci provided by the imaging system, adjust the relative phases so as to cause constructive interference of the ultrasound foci, thereby generating the global focus.

* * * * *